(12) United States Patent
Behbahani et al.

(10) Patent No.: US 12,226,654 B2
(45) Date of Patent: *Feb. 18, 2025

(54) DOSE RATE MONITOR, SYSTEM AND METHOD

(71) Applicant: Varian Medical Systems, Inc., Palo Alto, CA (US)

(72) Inventors: Reza Alibazi Behbahani, Mountain View, CA (US); Flavio Poehlmann-Martins, Fremont, CA (US)

(73) Assignee: Varian Medical Systems, Inc., Palo Alto, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/118,653

(22) Filed: Mar. 7, 2023

(65) Prior Publication Data

US 2023/0241413 A1 Aug. 3, 2023

Related U.S. Application Data

(63) Continuation of application No. 17/219,448, filed on Mar. 31, 2021, now Pat. No. 11,596,806.

(51) Int. Cl.
*A61N 5/10* (2006.01)
*G01T 1/02* (2006.01)

(52) U.S. Cl.
CPC .......... *A61N 5/1031* (2013.01); *A61N 5/1064* (2013.01); *A61N 5/1071* (2013.01); *G01T 1/02* (2013.01)

(58) Field of Classification Search
None
See application file for complete search history.

(56) References Cited

U.S. PATENT DOCUMENTS

| | | | |
|---|---|---|---|
| 3,398,282 A | 8/1968 | Rolf et al. | |
| 3,665,197 A | 5/1972 | Richter | |
| 11,596,806 B2* | 3/2023 | Behbahani | H01J 47/02 |
| 2012/0229143 A1* | 9/2012 | Otani | A61N 5/1077 |
| | | | 324/464 |
| 2014/0225094 A1* | 8/2014 | Fraboni | H10K 30/81 |
| | | | 438/82 |
| 2015/0338354 A1 | 11/2015 | Wu et al. | |
| 2017/0021198 A1 | 1/2017 | Kawrykow et al. | |
| 2020/0209410 A1* | 7/2020 | Kashiwa | H01J 47/02 |

FOREIGN PATENT DOCUMENTS

JP 2002-033071 A 1/2002

* cited by examiner

*Primary Examiner* — Hoon K Song
(74) *Attorney, Agent, or Firm* — Harness, Dickey & Pierce, P.L.C.

(57) ABSTRACT

A radiation dose rate monitor system includes an emitting electrode configured to be impinged by radiation radiation; a collecting electrode configured to form an electrical circuit with said emitting electrode, a current measurement device configured to measure a current through said emitting and collecting electrodes indicative of a dose of said radiation radiation, and a chamber enclosing a gas. Emission of secondary electrons from the emitting electrode provides a majority of the current.

20 Claims, 6 Drawing Sheets

```
START
  ↓
510 APPLY A VOLTAGE ACROSS A COMPLEMENTARY PAIR OF
ELECTRODES THAT ARE PART OF A DOSE RATE MEASUREMENT
CHAMBER
  ↓
520 COLLECT SECONDARY ELECTRONS AT THE PAIR OF ELECTRODES.
  ↓
530 MEASURE A CURRENT DUE TO THE SECONDARY ELECTRON
EMISSION TO INDICATE A DOSE RATE OF THE RADIOTHERAPY
RADIATION
  ↓
540 CONTROL DOSE RATE BASED ON THE INDICATION OF DOSE RATE
  ↓
End
```

DOSE RATE MONITOR, SYSTEM AND METHOD

RELATED APPLICATION(S)

This Application is a Continuation of commonly owned U.S. patent application Ser. No. 17/219,448, now U.S. Pat. No. 11,596,806, filed Mar. 31, 2021, which is incorporated herein by reference in its entirety.

FIELD OF INVENTION

Embodiments of the present invention relate to the field of medical devices. More specifically, embodiments of the present invention relate to systems and methods for measuring and monitoring dosage rates of therapeutic radiation.

BACKGROUND

External beam radiation therapy may be used in the treatment of various cancers and non-malignant conditions. Generally, ionizing radiation, including, for example, photons, e.g., X-rays, gamma rays, and charged particles, e.g., protons and electrons, is directed at an area of interest. In many cases, such ionizing radiation is generated by a linear accelerator or a cyclotron.

It is critical to accurately measure the dose of such radiation during treatment. For example, radiotherapy is typically very precisely planned based on numerous factors, including, for example, tumor type, tumor location, and stage, as well as the general health of the patient. In general, too much radiation may harm a patient, and too little radiation may not achieve a desired therapeutic effect.

Conventionally, an ionization chamber may be utilized to measure radiation dosage and/or dose rate based on radiation induced ionization in a gas. A sample gas is enclosed in an ionization chamber between two electrodes. The radiation "beam" is directed through the ionization chamber prior to impacting a patient, causing some of the sample gas to be ionized. The ionization typically creates a negatively charged electron and a positive ion. A voltage applied to the electrodes, for example 500 volts, collects the electrons on the positive electrode and collects positive ions on the negative electrode. A current collected by these electrodes is generally proportional to the radiation dose rate, and may be measured to create a dose monitor. As long as the radiation ionizes only a small fraction of the gas, the current will be linear with respect to dose rate.

FLASH radiotherapy is an emerging radiotherapy regime that appears to reduce radiation-induced toxicities while maintaining a tumor response similar to that of more conventional radiotherapy regimes. FLASH radiotherapy may be characterized as delivering a high radiation rate, e.g., greater than about 40 grays (Gy) per second, that allows for a total radiotherapy treatment dose, or large fractions of a total radiation dose, to be delivered in parts of a second, compared to several minutes for conventional radiotherapy. For example, a conventional radiotherapy treatment may include a total dose of 12-25 grays (Gy) delivered at a rate of up to 0.4 Gy/s, requiring minutes of treatment time. In contrast, FLASH radiotherapy may deliver a similar total dose at a rate of 40 Gy/s, requiring a fraction of a second of treatment time.

However, when radiation dose rates are very high, as is the case with FLASH radiotherapy, conventional dosage monitoring devices become less accurate than desired. Due to the high radiation intensity, a great many electron/ion pairs are created such that electrons and ions make up a significant fraction of the sample gas, and ions/electrons from different tracks encounter each other on their way to the collecting electrode(s). As a result, recombination between electrons and ions occurs at a high rate that varies with the dose rate, and the measured current no longer corresponds linearly to the radiation dose rate. Thus, conventional dosage monitoring devices are generally not accurate enough for use with FLASH radiotherapy.

SUMMARY OF THE INVENTION

Therefore, what is needed are systems and methods for radiotherapy dose rate monitoring. What is additionally needed are systems and methods for radiation dose rate monitoring that accurately measure doses of FLASH radiotherapy. Further, there is a need for systems and methods for radiation dose rate monitoring that accurately measure radiation doses of both conventional and FLASH radiation. There is a still further need for systems and methods for radiation dose rate monitoring that provide external ion chambers for dose verification and quality assurance. There is a yet further need for systems and methods for radiation dose rate monitoring that are compatible and complementary with existing systems and methods of radiation.

In accordance with an embodiment of the present invention, a radiotherapy dose rate monitor system includes a collecting electrode configured to be impinged by radiotherapy radiation; an emitting electrode configured to form an electrical circuit with said emitting electrode, and a current measurement device configured to measure a current through said emitting and collecting electrodes indicative of a dose of said radiotherapy radiation. Emission of secondary electrons from the emitting electrode provides a majority of the current.

According to a method embodiment, a method of measuring a radiation dose rate includes applying a voltage across a complementary pair of electrodes. At least one of the electrodes is exposed to a radiation beam. The method also includes collecting, at the electrodes, secondary electrons emitted from the electrodes in response to the radiation beam. The method further includes measuring a current due to the secondary electron emission to indicate the radiation dose rate.

According to another method embodiment, a method of monitoring a radiation dose rate includes applying a voltage across a complementary pair of electrodes. At least one of the electrodes is exposed to a radiation beam. The method also includes measuring current corresponding to a radiation dose rate in a first mode or in a second mode. In the first mode, more than 80 percent of the current is due to collection of secondary electrons, and in the second mode more than 80 percent of the current is due to collection of electron/ion pairs at electrodes due to ionization of a gas between the pair of electrodes.

BRIEF DESCRIPTION OF THE DRAWINGS

The accompanying drawings, which are incorporated in and form a part of this specification, illustrate embodiments of the invention and, together with the description, serve to explain the principles of the invention. Unless otherwise noted, the drawings may not be drawn to scale.

DETAILED DESCRIPTION

Reference will now be made in detail to various embodiments of the invention, examples of which are illustrated in the accompanying drawings. While the invention will be described in conjunction with these embodiments, it is understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the invention, numerous specific details are set forth in order to provide a thorough understanding of the invention. However, it will be recognized by one of ordinary skill in the art that the invention may be practiced without these specific details. In other instances, well known methods, procedures, components, and circuits have not been described in detail as not to unnecessarily obscure aspects of the invention.

Figure 5:
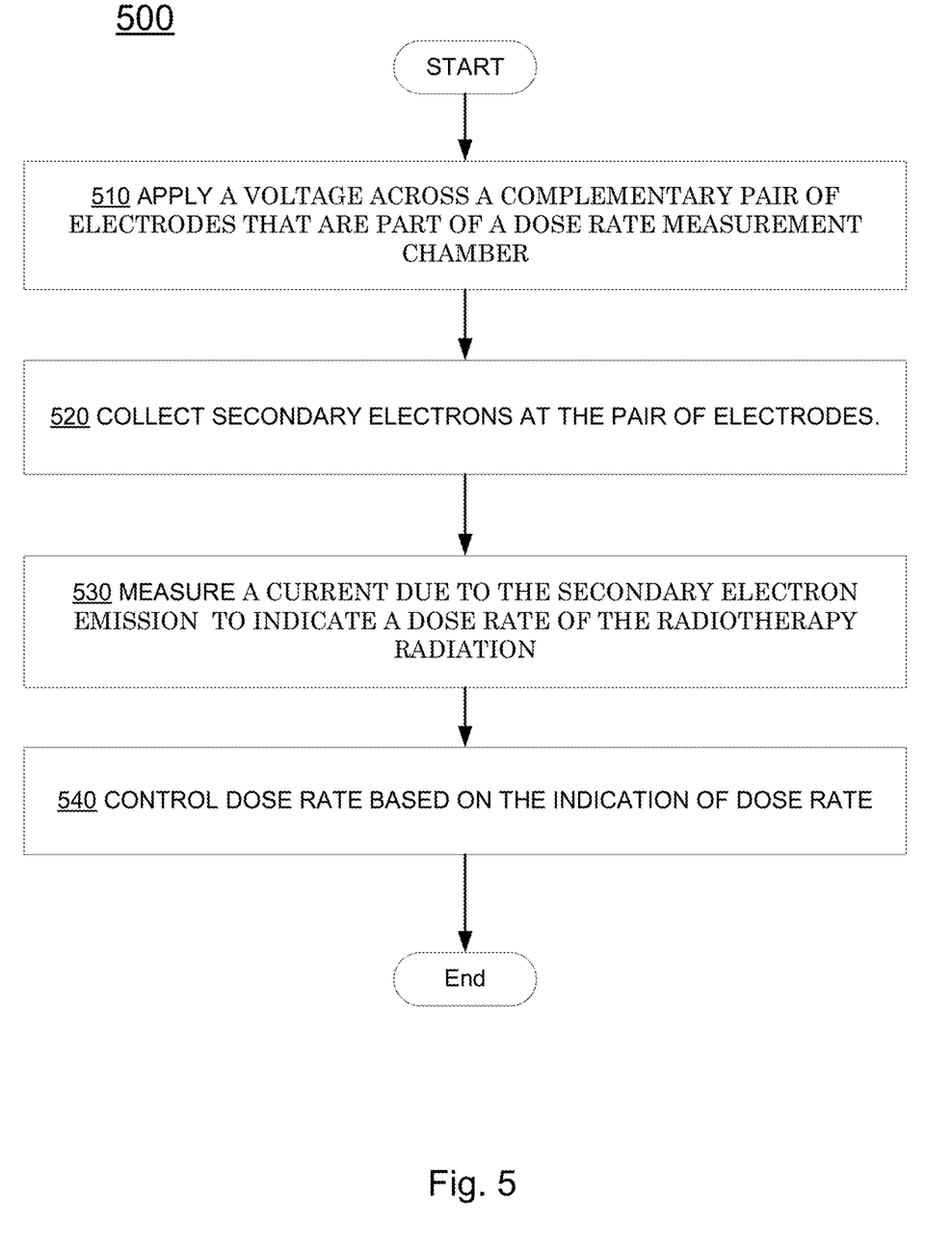
FIG. 5 is a simplified flowchart of an exemplary method of measuring a radiotherapy dose rate, in accordance with embodiments of the present invention.

Some portions of the detailed descriptions which follow (e.g., method 500) are presented in terms of procedures, steps, logic blocks, processing, and other symbolic representations of operations on data bits that may be performed on computer memory. These descriptions and representations are the means used by those skilled in the data processing arts to most effectively convey the substance of their work to others skilled in the art. A procedure, computer executed step, logic block, process, etc., is here, and generally, conceived to be a self-consistent sequence of steps or instructions leading to a desired result. The steps are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, data, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present invention, discussions utilizing terms such as "applying" or "controlling" or "generating" or "testing" or "heating" or "bringing" or "capturing" or "storing" or "reading" or "analyzing" or "resolving" or "accepting" or "selecting" or "determining" or "displaying" or "presenting" or "computing" or "sending" or "receiving" or "reducing" or "detecting" or "setting" or "accessing" or "placing" or "forming" or "mounting" or "removing" or "ceasing" or "stopping" or "coating" or "processing" or "performing" or "adjusting" or "creating" or "executing" or "continuing" or "indexing" or "translating" or "calculating" or "measuring" or "gathering" or "running" or the like, refer to the action and processes of, or under the control of, a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The meaning of "non-transitory computer-readable medium" should be construed to exclude only those types of transitory computer-readable media which were found to fall outside the scope of patentable subject matter under 35 U.S.C. § 101 in In re Nuijten, 500 F.3d 1346, 1356-57 (Fed. Cir. 2007). The use of this term is to be understood to remove only propagating transitory signals per se from the claim scope and does not relinquish rights to all standard computer-readable media that are not only propagating transitory signals per se.

In the following disclosure, exemplary embodiments in accordance with the present invention are illustrated in terms of a linear accelerator and radiotherapy photons, e.g., X-rays. However, it will be appreciated by those skilled in the art that the same or similar principles apply to other systems, including, for example, cyclotrons, and other types of ionizing radiation, including, for example, electrons, protons, and/or other particles. All such systems are well suited to, and are within the scope of embodiments in accordance with the present invention.

In the following descriptions, various elements and/or features of embodiments in accordance with the present invention are presented in isolation so as to better illustrate such features and as not to unnecessarily obscure aspects of the invention. It is to be appreciated, however, that such features, e.g., as disclosed with respect to a first drawing, may be combined with other features disclosed in other drawings in a variety of combinations. All such embodiments are anticipated and considered, and may represent embodiments in accordance with the present invention.

Dose Rate Monitor, System and Method

Figure 1:
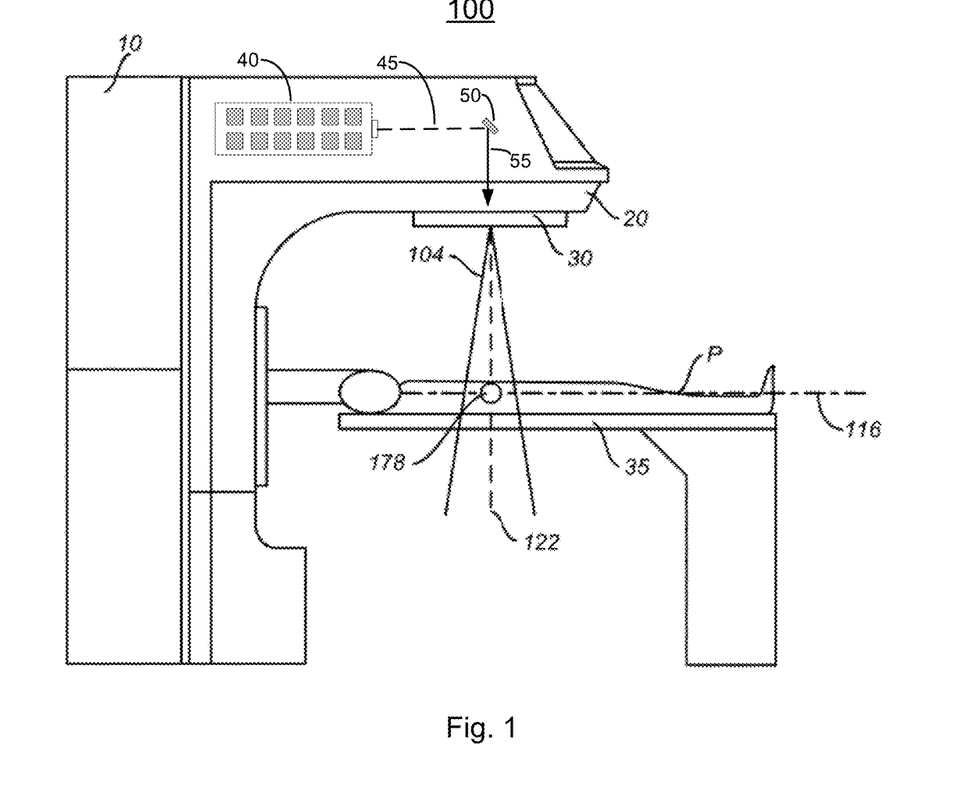
FIG. 1 illustrates a block diagram of an exemplary radiation treatment system that may serve as a platform for embodiments in accordance with the present invention.

FIG. 1 illustrates a block diagram of an exemplary radiation treatment system 100 that may serve as a platform for embodiments in accordance with the present invention. Radiation treatment system 100 may be similar to a TrueBeam® radiotherapy system, commercially available from Varian Medical Systems, Palo Alto, CA Stand 10 supports a rotatable gantry 20 with a treatment head 30. The treatment head 30 may extend into the gantry 20. In proximity to stand 10 there is arranged a control unit (not shown) which includes control circuitry for controlling the different modes of operation of the system 100.

Radiation treatment system 100 comprises a linear accelerator 40, for example, within gantry 20, utilized to create a radiation beam. Typically, radiation treatment system 100 is capable of generating either an electron (particle) beam or an x-ray (photon) beam for use in the radiotherapy treatment of patients on a treatment couch 35. Other radiation treatment systems are capable of generating heavy ion particles such as protons. For purposes of the following disclosure, only x-ray irradiation will be discussed.

A high voltage source is provided within the stand and/or in the gantry to supply voltage to an electron gun (not shown) positioned on an accelerator guide located in the gantry 20. Electrons are emitted from the electron gun into the accelerator 40 where they are accelerated. A source supplies radio frequency (microwave) power for the generation of an electric field within the waveguide. The electrons emitted from the electron gun are accelerated in the waveguide by the electric field, and exit the waveguide as a high-energy electron beam 45, for example, at megavoltage energies. The electron beam 45 then strikes a suitable metal target 50, emitting high energy x-rays 55 in the direction of a patient P.

As illustrated in FIG. 1, a patient P is shown lying on the treatment couch 35. X-rays formed as described above are emitted from the target in the treatment head 30 in a divergent beam 104. Typically, a patient plane 116, is positioned about one meter from the x-ray source or target, and the axis of the gantry 20 is located on the plane 116, such that the distance between the target and the isocenter 178 remains constant when the gantry 20 is rotated. The isocenter 178 is at the intersection between the patient plane 116 and the central axis of beam 122. A treatment volume to be irradiated is located about the isocenter 178.

Figure 2:
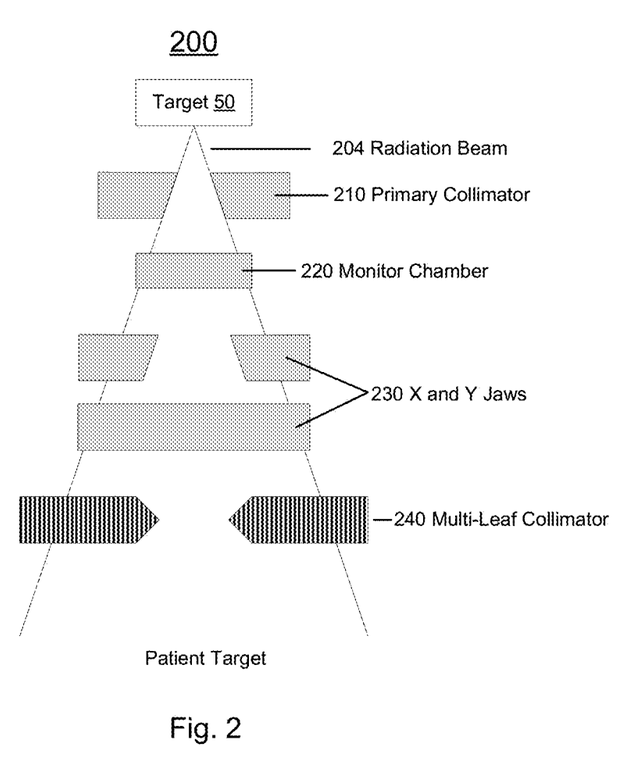
FIG. 2 illustrates a schematic of an exemplary beam path within an exemplary radiation treatment system, in accordance with embodiments of the present invention.

FIG. 2 illustrates a schematic of an exemplary beam path 200 within exemplary radiation treatment system 100, in accordance with embodiments of the present invention. It is appreciated that the illustrated components of beam path 200 are exemplary, and all may not be required in some embodiments. Additional components, e.g., a flattening filter (not shown), may also be included in accordance with embodiments of the present invention. A radiation beam 204 passes through primary collimator 210, X and Y jaws 230, and multi-leaf collimator 240. The primary collimator may comprise a plurality of selectable collimators and/or filters, in some embodiments. The primary collimator, X and Y jaws 230, and the leaves of the multi-leaf collimator (MLC) 240 typically comprise an x-ray blocking material, and are positioned in the head 30 (FIG. 1) to define the width of the x-ray beam at the patient plane. Typically, the X and Y jaws 230 are moveable and, when fully open, define a maximum beam width at the patient plane 116 (FIG. 1). The MLC 330 is positioned at the exit of the head 30, to further shape the x-ray beam. Exemplary MLCs may use up to 120 individually controllable leaves, for example, thin slices of tungsten, which may be moved into or out of the x-ray beam under the control of system software.

In accordance with embodiments of the present invention, a monitor chamber 220 is placed within radiation beam 204. Generally, monitor chamber 220 may be placed between a primary collimator 210 and X and Y jaws 230, although that is not required. Monitor chamber 220 is utilized to measure the radiation dose delivered by radiation beam 204.

Figure 3A:
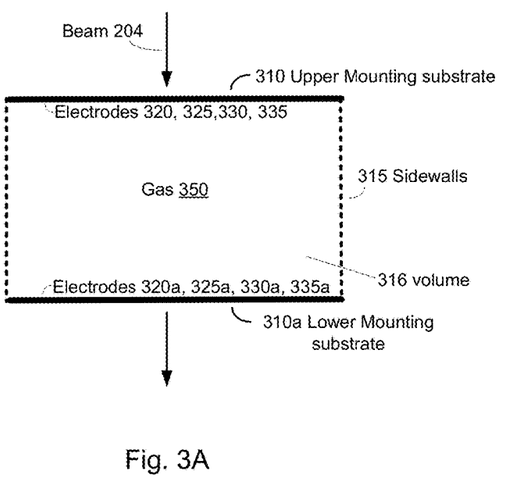
FIGS. 3A and 3B illustrate an exemplary monitor chamber, in accordance with embodiments of the present invention.
Figure 3B:
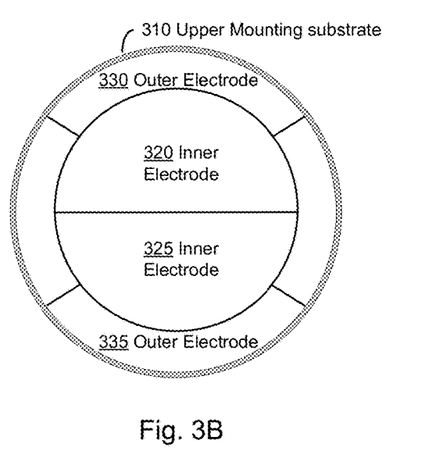

FIGS. 3A and 3B illustrate an exemplary monitor chamber 220, in accordance with embodiments of the present invention. Monitor chamber 220 may be utilized, for example, in radiation treatment system 100, to measure a radiation dose and/or dose rate, for example. Monitor chamber 220 typically provides closed loop feedback to portions of radiation treatment system 100 (FIG. 1) to control the intensity of beam 204. Monitor chamber 220 typically also provides a record of a treatment dose. Monitor chamber 220 may further function as part of an emergency shut off capability if a safe and/or a prescribed level of radiation is exceeded. At least a portion of monitor chamber 220 is positioned within radiation beam 204, as illustrated in FIG. 2. FIG. 3A illustrates a side-sectional view of an exemplary monitor chamber 220, in accordance with embodiments of the present invention.

Monitor chamber 220 may be cylindrical, although that is not required. Monitor chamber 220 is well suited to a wide variety of shapes, including shapes having regular and irregular cross sections. For example, monitor chamber 220 may have a square, rectangular, or hexagonal cross section, in some embodiments. As illustrated in FIG. 3A, monitor chamber 220 comprises at least one pair of complementary electrodes, for example, electrode 320 and electrode 320a. The complementary pair(s) of electrodes forms an electrical circuit. In some embodiments, one or more of the complementary pair(s) of electrodes may be mounted to or on upper mounting substrate 310 and/or lower mounting substrate 310a, coupled together by sidewall(s) 315. In some embodiments, one or more of the complementary pair(s) of electrodes may form or be mounted to other structures.

Monitor chamber 220 generally encloses a gas. For example, the volume 316 enclosed by upper mounting substrate 310, lower mounting substrate 310a, and sidewall 315 comprises a gas 350. In some embodiments, gas 350 may be sealed within volume 316, e.g., gas 350 is constrained from exchanging with an atmosphere outside of volume 316. In some embodiments, volume 316 is not so sealed. It is generally desirable for the mounting substrates 310, 310a and associated electrodes to be highly transparent to radiation beam 204. For example, such components may be characterized as being thin and of limited mechanical strength. Such mechanical constrains may limit a range of pressures for gas 350, and/or contribute to a requirement for mounting electrodes on substrates. Gas 350 may be below, at, or above ambient atmospheric pressure, in some embodiments.

FIG. 3B illustrates a plan view of an exemplary arrangement of four electrodes on the inner surface of upper mounting substrate 310, in accordance with embodiments of the present invention. Embodiments in accordance with the present invention are well suited to more or fewer electrodes, as well as to different shape(s) and orientations of electrodes. The electrodes need not be substantially planar shapes, as illustrated in FIG. 3B. For example, in accordance with embodiments of the present invention, one or more electrodes may comprise three dimensional structures, including, for example, wires, rods, bars, cups, cones, and/or mesh shapes. It is appreciated that all electrodes are not required to be the same shape, in some embodiments.

A plan view of electrode(s) of lower mounting substrate 310a is not illustrated, but may be a mirror image to that of upper mounting substrate 310. As will be further described below, electrodes of the upper mounting substrate 310 are paired with corresponding electrodes of the lower mounting substrate 310a (or elsewhere) to form an electrical circuit. For example, electrode 320 of upper mounting substrate 310 is paired with electrode 320a (FIG. 3A) of lower mounting substrate 310a to form an electrical circuit.

Exemplary upper mounting substrate 310 and exemplary lower mounting substrate 310a may be configured to be perpendicular to, and incident to radiation beam 204, although that is not required. For example, one or more substrates 310, 310a and/or electrodes 320, 320a, 325, 325a, 330, 330a, 335, 335a (FIG. 3A) may not be perpendicular to radiation beam 204, in some embodiments. Further, one or more substrates 310, 310a and/or electrodes 320, 320a, 325, 325a, 330, 330a, 335, 335a (FIG. 3A) are not required to be parallel with one another, in some embodiments. For example, sidewall 315 (FIG. 3A) may not be perpendicular to radiation beam 204 and may not be parallel with another electrode. Sidewall 315 may form, or support an electrode. In addition, the collecting electrode is not required to be within the radiation beam 204, in some embodiments. In general, radiation beam 204 may be configured to pass through at least a portion of volume 316.

Exemplary upper mounting substrate 310 comprises four electrodes: inner electrode 320, inner electrode 325, outer electrode 330, and outer electrode 335. The inner electrodes, 320 and 325, may be configured to be completely within the incident radiation beam 204. The inner electrodes, 320 and 325, are configured to measure a total dose rate of the incident radiation beam 204. Any dose rate difference between inner electrodes 320 and 325 may reveal a beam 204 angle symmetry error.

The outer electrodes, 330 and 335, may be configured to be partially within the beam 204, e.g., on an edge of beam 204. Any dose rate difference between outer electrodes 330 and 335 may reveal a beam 204 position symmetry error.

Figure 4:
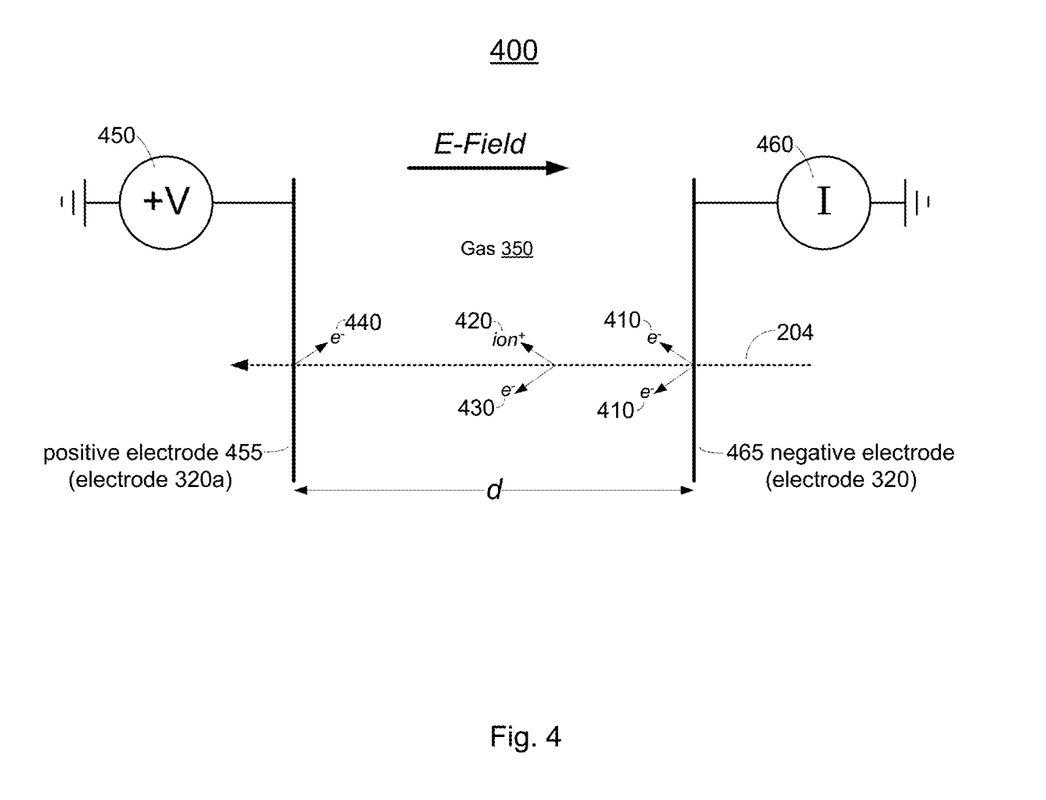
FIG. 4 illustrates a schematic diagram of an exemplary pair of corresponding electrodes as part of a monitor unit, in accordance with embodiments of the present invention.

FIG. 4 illustrates a schematic diagram of an exemplary pair of corresponding complementary electrodes as part of a monitor unit 220, in accordance with embodiments of the present invention. Monitor unit 220 comprises positive electrode 455, which may also be known as or referred to as a collecting electrode, for example, electrode 320a on lower mounting substrate 310a (FIG. 3A). Monitor unit 220 also comprises negative electrode 465, which may also be known as or referred to as an emitting electrode, for example, electrode 320 on upper mounting substrate 310 (FIG. 3A). The terms positive electrode and negative electrode refer to the relative electrical potential of the electrodes relative to one another. Only a single pair of complementary electrodes, e.g., electrodes 320 and 320a, is illustrated. Other pairs of complementary electrodes, e.g., electrode pair 325 and 325a, electrode pair 330 and 330a, and/or electrode pair 335 and 335a (FIG. 3A), if present, are configured similarly, and function in a similar manner.

A voltage source 450 applies a potential difference +V across the positive electrode 455 and negative electrode 465 in some embodiments. In some embodiments, a potential difference may be shifted, e.g., −V may be applied to the negative electrode 465, relative to the positive electrode 455, when the positive electrode 455 is at ground potential, for example. In some embodiments, a potential difference may be divided among the electrodes, e.g., +V/2 is applied to the positive electrode 455, and −V/2 is applied to the negative electrode 465. A voltage split may be uneven in some embodiments.

It is appreciated that radiation beam 204 will generally have greater extent than illustrated. For example, radiation beam 204 may be as wide, or wider, than the electrodes 455, 465, in some embodiments. Radiation beam 204 passing through gas 350 causes some of gas 350 to ionize, creating positive ions 420 and negative electrons 430. In addition, radiation beam 204 produces secondary electrons 410 via interaction with the conductive material of negative electrode 465, and produces secondary electrons 440 via interaction with the conductive material of positive electrode 455.

Radiotherapy is typically delivered in very short pulses. For example, a conventional radiotherapy system may deliver 360 pulses per second, with each pulse having a duration of about 4 µs. Each pulse may provide a dose of about 1 mGy, for example. Such an exemplary protocol delivers about 0.4 Gy/s on a time average basis. FLASH radiotherapy may be characterized as delivering a radiation dose greater than or equal to 40 grays (Gy) per second, on a time average basis.

Under the conventional art, the potential difference between electrodes may be on the order of 500 volts when the electrodes 455, 465 are separated by a gap d of about 1.0 mm, yielding an electric field of about 500,000 volts/m. When such a voltage is applied, an electrical current through a monitor unit, e.g., as measured by current sensor 460, is dominated by the ionization of gas 350. For example, negative electrons 430 are collected on the positive or collecting electrode 455, and positive ions 420 are collected on the negative electrode 465. Under the conventional art, the secondary electrons 410, 440, do not substantially contribute to current. For example, secondary electrons 410, 440 contribute less than 10% to the current.

At high radiation intensities, e.g., equal to or greater than about 2 mGy per 4 µs pulse, a great many electron 430/ion 420 pairs are created, such that electrons 430 and ions 420 make up a significant fraction of the sample gas. As a result, recombination between electrons 430 and ions 420 occurs at a high rate, and the measured current no longer corresponds linearly to the radiation dose rate. Thus, conventional dosage monitoring devices are generally not accurate enough for use with high intensity and/or FLASH radiotherapy. For example, such conventional dosage monitoring devices are generally not able to achieve greater than or equal to 98% accuracy in reporting high intensity and/or FLASH radiotherapy dose rates. Accuracy may be determined in comparison to other well-known dosimeter devices that are typically not used during treatment, including, for example, external probes and/or film dosimeters.

In accordance with embodiments of the present invention, voltage source 450 may generate a voltage between electrodes 455, 465 that is sufficient to repel secondary electrons emitted from an electrode from collecting on an electrode, and low enough that ion pairs recombine in the gas 350 and do not collect on an electrode.

In accordance with embodiments of the present invention, voltage source 450 may generate a voltage of 10-100 volts, for example, 40 volts, across the electrodes 455, 465, separated by a gap d of about 1.0 mm. Such combinations of voltages and separation distances result in electric field strengths of 10,000 volts/m to 100,000 volts/m. Other voltage and separation combinations producing such a range of electric field strengths may be utilized in some embodiments. It is appreciated that such a voltage and/or field strength is about an order of magnitude less than is typically applied under the conventional art for a similar separation between electrodes. Under such a reduced voltage, in accordance with embodiments of the present invention, ionization of the monitor chamber fill gas 350 does not contribute significantly to the collected charge. A low bias +V voltage, for example, around 40 volts for a 1.0 mm gap, for an electric field strength of about 40,000 volts/m, between the electrodes 455 and 465, causes and/or allows the ions 420 and electrons 430 to recombine almost immediately. Accordingly, the ions 420 and electrons 430 generally do not collect on the electrodes 465 and/or 455, resulting in an ion collection efficiency of almost zero. For example, ions 420 and electrons 430 contribute less than half of the current.

In accordance with embodiments of the present invention, the desirable repulsion of secondary electrons emitted from the electrodes is primarily a function of the voltage applied between electrodes. Thus, higher voltages promote greater repulsion of secondary electrons from the electrodes. In contrast, lower electric fields are beneficial to promoting the desirable fast recombination of ionized gas molecules such that electron/ion pairs rapidly recombine and do not contribute to current. Accordingly, in accordance with embodiments of the present invention, it may be beneficial to increase a gap dimension between complementary electrode pairs in order to decrease an electric field between electrodes while maintaining a desirably high electrical potential between electrodes, for example, increasing a gap size to about 4 mm for a 40 volt bias voltage.

In accordance with embodiments of the present invention, it may be beneficial to use a gas 350 in a dose monitoring system 220 having a higher ionization recombination coefficient and/or a higher electronegativity than ordinary air, for example, a gas comprising a higher concentration of oxygen, $O_2$, than air, including pure oxygen, and/or a gas comprising fluorine, including, for example, sulfur hexafluoride, $SF_6$. Such a higher ionization recombination coefficient and/or a higher electronegativity contributes to faster recombination of separated ions, beneficially further reducing a contribution of positive ions 420 and negative electrons 430 to current.

In accordance with embodiments of the present invention, an electrical current through current sensor 460 is substantially due to the interaction of the high intensity radiation beam 204 with the conductor material of the negative or emitting electrode 465. Radiation beam 204 knocks out some secondary electrons (SE) 410 with energy of about 40 eV from the negative electrode 465. Thus, a negative potential of about 40 volts is sufficient to repel such electrons from the negative electrode 465. Due to the negative potential of electrode 465, the emitted electrons are repelled and do not return to the negative electrode 465, but rather are replaced by current in the electrical circuit. This current I, which represents the total released electron charge from the surface of negative electrode 465, is proportional to beam dose rates. Electrons 440 knocked out from positive electrode 455 will combine with ions 420 and/or return to the positive or collecting electrode 455, and do not make up a significant portion of the current. In electron therapy, the measured current is related to the electron beam current and energy. The total electron charge may be used for measuring electron beam current with well-defined electron beam energy. Thus, the total secondary electron charge may be used to measure the delivered dose to a patient at any depth.

Embodiments in accordance with the present invention utilize a much lower voltage and/or a much lower electric field across electrodes in a dose monitor system, and utilize a different mechanism of current generation with such electrodes, in comparison with the conventional art. For example, current generation under the conventional art is dominated by ionized gas. In contrast, in accordance with embodiments of the present invention, current generation is dominated by the emission of secondary electrons from the negative, or emitting, electrode. In this novel manner, embodiments in accordance with the present invention are able to accurately measure high radiation dose rates, e.g., dose rates equal to or greater than about 2 mGy per 4 μs pulse, or about 0.7 Gy/s on a time average basis, including dose rates of FLASH radiotherapy. For example, embodiments in accordance with the present invention may achieve an accuracy of greater than or equal to 98% for high intensity and/or FLASH radiotherapy dose rates.

Referring once again to FIG. 1, many conventional radiotherapy systems are designed to rotate around the isocenter 178 of patient P, in order to distribute a radiation dose over all of the surrounding tissue while delivering an entire dose to the target tissue. One potential benefit of FLASH radiotherapy is that it appears to reduce radiation-induced damage to surrounding tissues while maintaining a tumor response equivalent to that of more conventional radiotherapy regimes. This benefit of FLASH radiotherapy may reduce the benefit(s) of such rotation. Embodiments in accordance with the present invention provide systems and methods of accurately measuring dose and/or dose rates of FLASH radiotherapy. Accordingly, embodiments in accordance with the present invention may facilitate non-rotational FLASH radiotherapy, beneficially reducing the cost, complexity, and room-size requirements of such radiotherapy systems.

FIG. 5 is a simplified flowchart of an exemplary method 500 of measuring a radiotherapy dose rate, in accordance with embodiments of the present invention. Method 500 may be performed wholly or partially with a computer system, e.g., computer system 600 of FIG. 6.

In 510, a voltage is applied across a complementary pair of electrodes, e.g., electrodes 455, 465 (FIG. 4), that are part of a dose rate measurement chamber, e.g., dose rate measurement chamber 220 (FIG. 2). The radiotherapy radiation may be at dose rate intensities corresponding to FLASH radiotherapy. The voltage may be applied during a pulse of radiotherapy radiation, in some embodiments. In some embodiments, the voltage may be changed and/or removed when radiotherapy radiation is not present, for example, between radiation pulses.

In accordance with embodiments of the present invention, voltage source may be configured to apply a potential difference between the complementary pair of electrodes sufficient to repel secondary electrons. In some embodiments, the applied voltage may be between 30-100 volts. In some embodiments, the voltage source may be configured to generate an electric field between the complementary pair of electrodes such that electrons and ions of a gas within the dose rate measurement chamber that are ionized by the radiotherapy radiation recombine and do not contribute to current between the complementary pair of electrodes. In some embodiments, the electric field strength may be between 10,000-100,000 volts/m.

In 520, secondary electrons emitted from the electrodes are collected by the electrodes. It is appreciated that electrons and ions of a gas within the dose rate measurement chamber that are ionized by the radiotherapy radiation recombine and do not collect at the complementary pair of electrodes. In 530, a current due to the secondary electron emission is measured to indicate a dose rate of the radiotherapy radiation.

In optional 540, the indication of dose rate is used as feedback to control a dose rate of FLASH radiotherapy.

Figure 6:
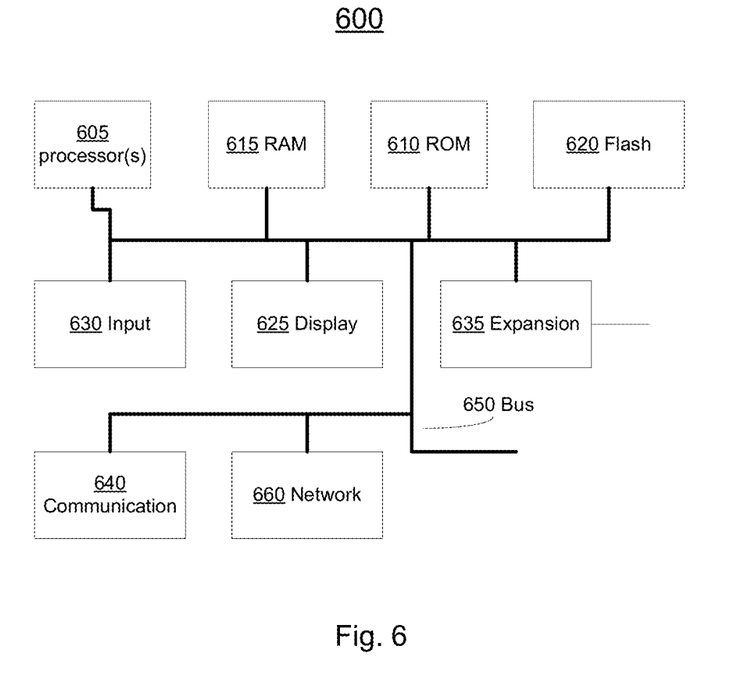
FIG. 6 illustrates a block diagram of an exemplary electronic system, which may be used as a platform to implement and/or as a control system for embodiments of the present invention.

FIG. 6 illustrates a block diagram of an exemplary electronic system 600, which may be used as a platform to implement and/or as a control system for embodiments of the present invention. Electronic system 600 may be a "server" computer system, in some embodiments. Electronic system 600 includes an address/data bus 650 for communicating information, a central processor complex 605 functionally coupled with the bus for processing information and instructions. Bus 650 may comprise, for example, a Peripheral Component Interconnect Express (PCIe) computer expansion bus, industry standard architecture (ISA), extended ISA (EISA), MicroChannel, Multibus, IEEE 796, IEEE 1196, IEEE 1496, PCI, Computer Automated Measurement and Control (CAMAC), MBus, Runway bus, Compute Express Link (CXL), and the like.

Central processor complex 605 may comprise a single processor or multiple processors, e.g., a multi-core processor, or multiple separate processors, in some embodiments. Central processor complex 605 may comprise various types of well-known processors in any combination, including, for example, digital signal processors (DSP), graphics processors (GPU), complex instruction set (CISC) processors, reduced instruction set (RISC) processors, and/or very long word instruction set (VLIW) processors. In some embodiments, exemplary central processor complex 605 may comprise a finite state machine, for example, realized in one or more field programmable gate array(s) (FPGA), which may operate in conjunction with and/or replace other types of processors to control embodiments in accordance with the present invention.

Electronic system 600 may also include a volatile memory 615 (e.g., random access memory RAM) coupled with the bus 650 for storing information and instructions for the central processor complex 605, and a non-volatile memory 610 (e.g., read only memory ROM) coupled with the bus 650 for storing static information and instructions for the processor complex 605. Electronic system 600 also optionally includes a changeable, non-volatile memory 620 (e.g., NOR flash) for storing information and instructions for the central processor complex 605 which can be updated after the manufacture of system 600. In some embodiments, only one of ROM 610 or Flash 620 may be present.

Also included in electronic system 600 of FIG. 6 is an optional input device 630. Device 630 can communicate information and command selections to the central processor 600. Input device 630 may be any suitable device for communicating information and/or commands to the electronic system 600. For example, input device 630 may take the form of a keyboard, buttons, a joystick, a track ball, an audio transducer, e.g., a microphone, a touch sensitive digitizer panel, eyeball scanner, and/or the like.

Electronic system 600 may comprise a display unit 625. Display unit 625 may comprise a liquid crystal display (LCD) device, cathode ray tube (CRT), field emission device (FED, also called flat panel CRT), light emitting diode (LED), plasma display device, electro-luminescent display, electronic paper, electronic ink (e-ink) or other display device suitable for creating graphic images and/or alphanumeric characters recognizable to the user. Display unit 625 may have an associated lighting device, in some embodiments.

Electronic system 600 also optionally includes an expansion interface 635 coupled with the bus 650. Expansion interface 635 can implement many well known standard expansion interfaces, including without limitation the Secure Digital Card interface, universal serial bus (USB) interface, Compact Flash, Personal Computer (PC) Card interface, CardBus, Peripheral Component Interconnect (PCI) interface, Peripheral Component Interconnect Express (PCI Express), mini-PCI interface, IEEE 1394, Small Computer System Interface (SCSI), Personal Computer Memory Card International Association (PCMCIA) interface, Industry Standard Architecture (ISA) interface, RS-232 interface, and/or the like. In some embodiments of the present invention, expansion interface 635 may comprise signals substantially compliant with the signals of bus 650.

A wide variety of well-known devices may be attached to electronic system 600 via the bus 650 and/or expansion interface 635. Examples of such devices include without limitation rotating magnetic memory devices, flash memory devices, digital cameras, wireless communication modules, digital audio players, and Global Positioning System (GPS) devices.

System 600 also optionally includes a communication port 640. Communication port 640 may be implemented as part of expansion interface 635. When implemented as a separate interface, communication port 640 may typically be used to exchange information with other devices via communication-oriented data transfer protocols. Examples of communication ports include without limitation RS-232 ports, universal asynchronous receiver transmitters (UARTs), USB ports, infrared light transceivers, ethernet ports, IEEE 1394, and synchronous ports.

System 600 optionally includes a network interface 660, which may implement a wired or wireless network interface. Electronic system 600 may comprise additional software and/or hardware features (not shown) in some embodiments.

Various modules of system 600 may access computer readable media, and the term is known or understood to include removable media, for example, Secure Digital ("SD") cards, CD and/or DVD ROMs, diskettes and the like, as well as non-removable or internal media, for example, hard drives, solid state drive s (SSD), RAM, ROM, flash, and the like.

Embodiments in accordance with the present invention provide systems and methods for radiotherapy dose rate monitoring. In addition, embodiments in accordance with the present invention provide systems and methods for radiotherapy dose rate monitoring that accurately measure radiotherapy doses of FLASH radiotherapy. Further, embodiments in accordance with the present invention provide systems and methods for radiotherapy dose rate monitoring that accurately measure radiotherapy doses of both conventional radiotherapy and FLASH radiotherapy. Still further embodiments in accordance with the present invention provide systems and methods for radiotherapy dose rate monitoring that provide external ion chambers for dose verification and quality assurance. Yet further, embodiments in accordance with the present invention provide systems and methods for radiotherapy dose rate monitoring that are compatible and complementary with existing systems and methods of administering radiotherapy.

Although the invention has been shown and described with respect to a certain exemplary embodiment or embodiments, equivalent alterations and modifications will occur to others skilled in the art upon the reading and understanding of this specification and the annexed drawings. In particular regard to the various functions performed by the above described components (assemblies, devices, etc.) the terms (including a reference to a "means") used to describe such components are intended to correspond, unless otherwise indicated, to any component which performs the specified function of the described component (e.g., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application.

Various embodiments of the invention are thus described. While the present invention has been described in particular embodiments, it should be appreciated that the invention should not be construed as limited by such embodiments, but rather construed according to the below claims.

We claim:

1. A radiation dose rate monitor system comprising:
   a collecting electrode configured to be impinged by radiation;
   an emitting electrode configured to form an electrical circuit with said collecting electrode; and
   a current measurement device configured to measure a current through said emitting electrode and said collecting electrode, the current being indicative of a dose of said radiation, wherein emission of secondary electrons from said emitting electrode provides a majority of said current.

2. The radiation dose rate monitor system of claim 1, wherein ionization of a gas contributes less than 20 percent of said current.

3. The radiation dose rate monitor system of claim 2, wherein said gas has a greater ionization recombination coefficient than air.

4. The radiation dose rate monitor system of claim 3, wherein said gas comprises oxygen at a higher concentration than that of air.

5. The radiation dose rate monitor system of claim 3, wherein said gas comprises fluorine.

6. The radiation dose rate monitor system of claim 1, further comprising:
a voltage source coupled between said emitting electrode and said collecting electrode,
wherein said voltage source is configured to apply a potential difference between said emitting electrode and said collecting electrode sufficient to repel said secondary electrons.

7. The radiation dose rate monitor system of claim 1, wherein the radiation dose rate monitor system is configured to generate an electric field between said emitting electrode and said collecting electrode such that electrons and ions from ionization of said gas recombine and do not contribute to current between said emitting electrode and said collecting electrode.

8. A method of measuring a radiation dose rate, the method comprising:
applying a voltage across a complementary pair of electrodes, wherein at least one of said electrodes is exposed to a radiation beam;
collecting, at the electrodes, secondary electrons emitted from the electrodes in response to the radiation beam; and
measuring a current due to emission of the secondary electron to indicate the radiation dose rate.

9. The method of claim 8, wherein said current is primarily due to collection of secondary electrons on one of said pair of electrodes.

10. The method of claim 8, further comprising a gas between said pair of electrodes, wherein said gas has a greater electronegativity than air.

11. The method of claim 10, wherein said gas has a greater ionization recombination coefficient than air.

12. The method of claim 10, further comprising:
generating an electric field between said pair of electrodes such that electrons and ions of said gas ionized by said radiation recombine and do not contribute to current between said complementary pair of electrodes.

13. The method of claim 8, wherein the applying a voltage includes
applying a potential difference between said pair of electrodes sufficient to repel said secondary electrons from an emitting electrode of said pair of electrodes.

14. A method of monitoring a radiation dose rate, the method comprising:
applying a voltage across a complementary pair of electrodes, wherein
at least one of said electrodes is exposed to a radiation beam; and
measuring current corresponding to a radiation dose rate in a first mode or in a second mode,
wherein, in said first mode, more than 80 percent of said current is due to collection of secondary electrons, and
wherein, in said second mode, more than 80 percent of said current is due to collection of electron/ion pairs at electrodes due to ionization of a gas between said pair of electrodes.

15. The method of claim 14, wherein said first mode corresponds to a dose rate characteristic of FLASH radiation.

16. The method of claim 14, wherein said second mode corresponds to a dose rate of less than 40 Gy/s.

17. The method of claim 14, wherein said first mode is configured to place a potential of equal to or less than 100 volts across said complementary pair of electrodes.

18. The method of claim 17, wherein said first mode is configured to place a potential of greater than 10 volts across said complementary pair of electrodes.

19. The method of claim 14, further comprising:
generating, in said first mode, an electric field strength of equal to or less than 100,000 volts/min in a region between said complementary pair of electrodes.

20. The method of claim 19, further comprising:
generating, in said first mode, an electric field strength of greater than 10,000 volts/min in said region between said complementary pair of electrodes.

* * * * *